(12) United States Patent
Matsumoto et al.

(10) Patent No.: US 7,388,064 B2
(45) Date of Patent: Jun. 17, 2008

(54) STEREOREGULAR POLYMER AND MONOMER THEREOF AND PROCESS FOR PRODUCTION OF BOTH

(75) Inventors: Akikazu Matsumoto, Kawachinagano (JP); Toshihiro Tanaka, Yokohama (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/513,756

(22) PCT Filed: May 8, 2003

(86) PCT No.: PCT/JP03/05763

§ 371 (c)(1),
(2), (4) Date: Jun. 24, 2005

(87) PCT Pub. No.: WO03/095511

PCT Pub. Date: Nov. 20, 2003

(65) Prior Publication Data

US 2006/0009601 A1 Jan. 12, 2006

(30) Foreign Application Priority Data

May 9, 2002 (JP) ............................. 2002-134762

(51) Int. Cl.
*C08F 20/20* (2006.01)
(52) U.S. Cl. .................. 526/318.43; 560/22
(58) Field of Classification Search ........... 526/318.43; 560/122
See application file for complete search history.

(56) References Cited

OTHER PUBLICATIONS

A.Matsumoto et al. "Molecular Design and Polymer Structure Control Based on Polymer Crystal Engineering. Topochemical Polymerization of 1,3-Diene Mono- and Dicarboxylic Acid Derivatives Bearing a Naphthylmethylammonium Group as the Countercation", J. Am. Chem. Soc., 2000, vol. 122, No. 38, pp. 9109-9119.*

A.Matsumoto et al. "Crystal Engineering for Topochemical Polymerization of Muconic Esters Using Halogen-Halogen and CH/π Interactions as Weak Intermolecular Interactions", J. Am. Chem. Soc., 2002, vol. 124, No. 30, pp. 8891-8902.*

Koichi et al. "Preparation of Disyndiotactic Poly(methyl crotonate) by Stereospecific Group Transfer Polymerization", Polymer Journal, 1997, vol. 31, No. 2, pp. 177-183.*

Koichi Ute et. al, Preparation of Disyndiotactic Poly (methyl crotonate) by Stereospecific Group Transfer Polymerization, Polymer Journal, 1997, vol. 31, No. 2, 177-183.

Akikazu Matsumoto et. al, Stereospecific Polymerization of Dialkyl Muconates through Free Radical Polymerization: Isotropic Polymerization and Topochemical Polymerization, Macromolecules, 1996, vol. 29, 423-432.

Seishi Saragai et. al, Relationship between Packing Structure and Monomer Reactivity in the Photoinduced Solid-State Polymerizations of Muconic Diesters with Different Side Groups, J. Phys. Chem. B, 2001, vol. 105, 4155-4165.

"Photopolymerization of Diacetylenes", H. Bassler, Advances in Polymer Science 63, pp. 1-48 (1984).

"Photodimerization and Photopolymerization of Diolefin Crystals", M. Hasegawa, Advances in Physical Organic Chemistry vol. 30, pp. 117-171 (1995).

"Molecular Design and Polymer Structure control Based on Polymer Crystal Engineering. Topochemical Polymerization of 1,3-Diene Mono-and Dicarboxylic Acid Derivatives Bearing a Naphthylmethylammonium Group as the Countercation", A. Matsumoto, et al., J. Am. Chem. Soc. 20000, vol. 122, No. 38, pp. 9109-9119.

"Stereospecific Polymerization of 1,3-Diene Monomers in the Crystalline State", A. Matsumoto, Progress in Reaction Kinetics and Mechanism vol. 26, pp. 59-110 (2001).

"Stereospecific Polymerisation of Diethyl (Z,Z)-Hexa-2,4-dienedioate in the Crystalline State", A. Matsumoto et al., J. Chem. Soc., Chem. Commun., 1994, pp. 1389-1390.

\* cited by examiner

*Primary Examiner*—Randy Gulakowski
*Assistant Examiner*—M. Bernshteyn
(74) *Attorney, Agent, or Firm*—Nixon & Vanderhye P.C.

(57) ABSTRACT

An ester derivant having a crystal structure in which the molecules in two adjacent molecule planes are antiparallel is created from a carboxylic acid having carbon-carbon double bond and a compound having a functional group that can react to a carboxyl group of the carboxylic acid. The crystal of the ester derivant is then subjected to light irradiation or heating.

2 Claims, 12 Drawing Sheets

| | |
|---|---|
| Formula | $C_{22}H_{22}O_6$ |
| f.w. | 382.41 |
| crystal color habit | colorless plates |
| crystal system | monoclinic |
| space group | C2/c |
| $a$, Å | 36.026(3) |
| $b$, Å | 5.6019(4) |
| $c$, Å | 9.4840(7) |
| $\beta$, deg | 100.27(1) |
| $V$, Å$^3$ | 1883.4(2) |
| $Z$ | 4 |
| diffractometer | RAXIS |
| reflns measured | 7901 |
| unique reflns | 2151 |
| $R_{merge}$ | 0.087 |
| no observed($I > 2\sigma(I)$) | 1270 |
| no variables | 172 |
| parameter ratio | 7.38 |
| $R$ | 0.071 |
| $R_w$ | 0.117 |
| GOF | 1.01 |
| temp, °C | −70 |
| final diff four map (e Å$^{-3}$) | 0.32, −0.28 |

| | |
|---|---|
| Formula | EE4MeO C22H22O6 |
| f.w. | 382.41 |
| crystal color habit | colorless plates |
| crystal system | monoclinic |
| space group | C2/c |
| a, Å | 35.644(4) |
| b, Å | 5.6923(4) |
| c, Å | 9.7803(6) |
| $\beta$, deg | 100.533(3) |
| V, Å³ | 1951.0(2) |
| Z | 4 |
| diffractometer | RAXIS |
| reflns measured | 7791 |
| unique reflns | 2098 |
| $R_{merge}$ | 0.032 |
| no observed($I > 2\sigma(I)$) | 1726 |
| no variables | 166 |
| parameter ratio | 10.40 |
| R | 0.048 |
| $R_w$ | 0.100 |
| GOF | 0.95 |
| temp, °C | -70 |
| final diff four map (e Å⁻³) | 0.18, -0.26 |

| | |
|---|---|
| Formula | Poly(ZZ4MeO) $C_{22}H_{22}O_6$ |
| f.w. | 382.41 |
| crystal color habit | colorless plates |
| crystal system | monoclinic |
| space group | C2/c |
| $a$, Å | 35.117(4) |
| $b$, Å | 5.7980(6) |
| $c$, Å | 9.436(1) |
| $\beta$, deg | 99.321(2) |
| $V$, Å$^3$ | 1895.9(3) |
| Z | 4 |
| diffractometer | RAXIS |
| reflns measured | 6714 |
| unique reflns | 2151 |
| $R_{merge}$ | 0.033 |
| no observed($I > 2\sigma(I)$) | 1620 |
| no variables | 172 |
| parameter ratio | 9.42 |
| $R$ | 0.043 |
| $R_w$ | 0.071 |
| GOF | 0.89 |
| temp, °C | 23 |
| final diff four map (e Å$^{-3}$) | 0.21, -0.22 |

STEREOREGULAR POLYMER AND MONOMER THEREOF AND PROCESS FOR PRODUCTION OF BOTH

This application is the US national phase of International Application PCT/JP03/05763 filed 8 May 2003 which designated the U.S. and claims benefit of JP 134762/2002 dated 9 May 2002, the entire content of which is hereby incorporated by reference.

TECHNICAL FIELD

The present invention relates to a stereoregular polymer and monomer thereof, and process for production of both.

BACKGROUND ART

Physicalities of polymer depend on the primary structure of the polymer chain. Therefore, in the composition of polymer, the reaction structure is designed by controlling the primary structure, such as molecular mass of polymer, molecular mass distribution, terminal structure, branch structure, or stereo structure. In recent years, in addition to such a minute control of the primary structure of polymer chain, there has been a trend of controlling the higher-order structure, such as stereoregularity of polymer compound by controlling assembly of polymer chain, such as grouping, self-assembly, crystallization, or phase separation.

As an example of the control of higher-order structure, there is a method of using crystal lattice with a specific molecular sequence of the reaction field for polymerization reaction. More specifically, when using a monomer molecule in crystallization state, since the monomer molecule itself has a reaction field of the polymerization reaction, a stereoregular polymer can be produced by proceeding polymerization reaction, with minimum movement of atoms or substituent, without changing position of center of gravity of each monomer molecule, or symmetry of the crystal in polymerization reaction. Such polymerization reaction is called topochemical polymerization.

The reaction path and reaction speed of topochemical polymerization depend on the crystal structure, that is an aggregation of monomer molecules, and the structure of the resultant polymer is determined depending on the molecular sequence of the crystal. Further, producing a polymer through the topochemical polymerization makes it possible to obtain a polymer without separation or purification, and also, since the process may be done without an organic solvent, it causes less environmental burden.

The foregoing method of proceeding the topochemical polymerization under the control of crystal lattice allows easy production of a stereoregular polymer. With this finding, there have been active studies of the topochemical polymerization with the reports about solid-phase polymerization of diacetylene (Document: H. Basser, Adv. Polym. Sci., 63, p. 1 (1984) etc.), and solid-phase polymerization of olefin (Document: M. Hasegawa, Adv. Phys. Org. Chem., 30, p. 117(1995) etc.) etc. Further, the inventors of the present invention have reported topochemical polymerization of diene monomer (Document: A. Matsumoto, T. Matsumura, S. Aoki, J. Chem. Soc., Chem. Commun., 1994, p. 1389).

The topochemical polymerization of diene monomer is explained below with an example, (Z, Z)-1,4-butadiene (hereinafter referred to as diene monomer) having substituents $Y_1$ and $Y_2$, shown in FIGS. 11 and 12. Note that, the substituents $Y_1$ and $Y_2$ are identical in this example.

As shown before the arrow of FIG. 11, the diene monomer has a crystal structure in which all the monomer molecules are aligned in the same direction in a column. More specifically, when viewing the plane (molecular plane) having the monomer molecules from one side of the lamination direction (column direction), all the monomer molecules in the molecular plane face the same direction. In other words, if assuming the molecule plane from one side of the lamination direction is the upper surface, all the molecular planes formed by the monomer molecules are stacked showing upper surfaces.

Therefore, when topochemical polymerization occurs in the diene monomer, the diene monomers of FIG. 11 are bonded together at the positions denoted by the broken line, thus producing a polymer. As shown in FIG. 11, the produced polymer (diene polymer) has repeating units:—$CHY_1$—CH=CH—$CHY_2$—. The repeating units of each diene polymer have the same configuration in the vicinity of the carbons to which the substituents Y1 and Y2 are bonded. The polymer having this stereoregularity is called a diisotactic.

On the other hand, there exists an isomer of the diisotactic stereoregular polymer, having disyndiotactic structure. As mentioned above, the physicalities of polymer depend on the stereoregularity. Therefore, the polymer having the stereoregularity of disyndiotactic differs in crystallization, mechanical characteristic, solvent resistance, thermostability etc. from the diisotactic polymer.

As shown after the arrow in FIG. 12, the disyndiotactic structure polymer has such a stereoregularity that the repeating units of —CHY1-CH=CH—CHY2- in the vicinity of the carbons to which the substituents Y1 and Y2 are bonded are alternately identical. More specifically, in the disyndiotactic polymer, the two adjacent units have different configurations in the vicinity of the carbons to which the substituents Y1 and Y2 are connected. In other words, the disyndiotactic polymer has repeating units in which two kinds of units with different configurations alternately appear with a certain cycle.

To obtain such a disyndiotactic polymer through topochemical polymerization, as shown before the arrow of FIG. 12, there has been a technique of stacking the molecular planes so that the upper surface and the rear surface alternately appear (Document: A. Matsumoto, S. Nagahama, T. Odani, J. Am. Chem. Soc., 122, p. 9109(2000); A. Matsumoto, Prog. React. Kinet. Mecha., 26, p. 59 (2001) etc). More specifically, when viewing the planes (molecular plane) having the monomer molecules from one side of the lamination direction, the direction of the monomer molecules in the molecular plane is alternately identical. Further, by causing topochemical polymerization in the monomer molecules having such a crystal structure, a diene monomer is produced at the position denoted by the broken line in the figure. Further, it is assumed that a disyndiotactic polymer is also obtained, as shown after the arrow in FIG. 12.

However, there has been no report of actual acquirement of disyndiotactic polymer through the topochemical polymerization. More specifically, in prior art, there has been a proposal of obtaining a disyndiotactic polymer by using the monomer molecules having the structure shown in FIG. 12, but there is no report of successful acquirement of disyndiotactic polymer by using the diene monomer molecules shown in FIG. 12, or through topochemical polymerization of the diene monomer molecules.

The present invention is made in view of the foregoing conventional problems, and an object is to find the diene monomer having the structure of FIG. 12, and to provide a stereoregular polymer with disyndiotactic characteristic through polymerization of the diene monomer. The present invention further provides the manufacturing methods thereof.

DISCLOSURE OF INVENTION

In order to solve the foregoing problems, s stereoregular polymer of the present invention has a disyndiotactic structure with hydrocarbon chain repeating units each having at least one ester substituent.

The stereoregular polymer has such a structure that an atom (stereocenter hereinafter), constituting the main-chain and having a functional group such as an ester substituent, has a regular configuration. The regularity of the stereoregular polymer is disyndiotactic. In the disyndiotactic structure, the configurations of the stereocenters are not all identical but alternately identical in the repeating units. More specifically, in the disyndiotactic structure, the stereocenters of the adjacent repeating units have different configurations, and those adjacent units with different configurations constitute a unit in the iteration.

Examples of the stereoregular polymer of the present invention include a vinyl including repeating units of chain hydrocarbon having single bond between carbons, or a dien polymer containing double bond between carbons. Among these, a particularly preferred is a dien stereoregular polymer having a carbon-carbon double bond in the repeating units.

Further, the main chain of the repeating unit preferably has at least two substituents. The substituents may be both ester substituents or only one of them is an ester substituent. The unit may contain other substituents as long as it has at least one ester substituent. Accordingly, the monomer of the vinyl polymer is preferably a 1,2-di substitution product (α, δ-disubstitution product), and the monomer of the dien polymer is preferably a 1,4-di substitution product (α, δ-disubstitution product). Further, it may also be a derivant of the disubstituent or a multi-substitution product having more substituents in addition to these disubstituents.

The ester substituent is not particularly limited. For example, it may be an aster substituent with a function group of hydrocarbon group, halogenated hydrocarbon, amino group, or an aminoalkyl group. A most preferred is an ester substituent having a benzyl group containing ether bond.

Note that, the hydrocarbon group as a functional group is not limited, and may be either a saturated hydrocarbon group, or an unsaturated hydrocarbon group, and either a chain hydrocarbon group or a cyclic hydrocarbon group.

Specifically, the stereoregular polymer preferably has repeating units denoted by a general formula (1):

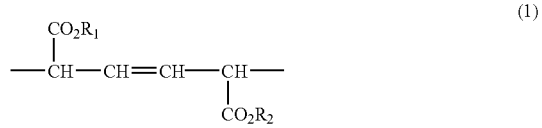

(1)

where $R_1$ and $R_2$ are hydrocarbon groups, each of which may have a functional group.

The functional group refers to a functional group other than the hydrocarbon group. The $R_1$ and $R_2$ are only required to be a hydrocarbon group having a functional group other than a hydrocarbon group. A preferred example is a benzyl group containing ether bond. Particularly referable examples for the ether bond in the benzyl group are $CH_3O$-(methoxy group), $C_2H_5O$-(ethoxy group), $C_3H_7O$-(propoxy group), $C_4H_9O$—(butoxy group), $C_6H_5O$-(phenoxy group).

Further, in the stereoregular polymer denoted by the general formula (1) above, the configuration at the carbon-carbon double bond preferably has a trans-configuration.

With this structure, the stereoregular polymer of the present invention, whose stereoregularity is disyndiotactic, is superior in crysterization, mechanical characteristic, solvent resistance thermostability than the polymer with diisotactic structure. Here, the polymer with diisotactic structure has repeating units having stereocenters with the same configurations.

More specifically, when used singly or as a polymer alloy combined with an existing polymer, the stereoregular polymer of the present invention becomes superior in thermostability, flame resistance, elasticity, pulling strength, flexural strength, shock-resistance, abrasion resistance, linear expansivity, dimensional stability, moldability, electric property, dielectric breakdown strength, permittivity, high-temperature property, antiweatherbility, or antihydrolytic.

The existing polymer to be combined with the stereoregular polymer of the present invention to create a polymer alloy may be a general-purpose polymer, a condensed polymer, an engineering plastic, a super engineer plastic or the like. For example, the general-purpose polymer may be polyolefine, dien polymer, vinyl polymer; and the condensed polymer may be polyester, polyamide, polyurethane etc. Further, engineering plastic or a super engineering plastic may be nylon, polyacetal, polycarbonate, denatured polyphenyleneoxide, polybutyleneterephthalate, polyethyleneterephthalate, polyphenylene sulfide, polysulfone, polyarylete, polyetherketone, polyimide etc.

The complexation to create polymer alloy may be performed through blending, IPN (Inter Penetrating Polymer Network), block grafting etc. Further, an inorganic material such as a glass fiber, carbon fiber may be mixed.

Therefore, the stereoregular polymer of the present invention may be used for electric, electronic material, injection molding circuit substrate, OA device component, magnetic disk, car outer panel, fuel-related component, electric-equipment-related component, car exterior equipment, car inner equipment, aircraft component, sport equipment, building material exterior, agricultural material, sundry goods, food wrapping etc.

Further, an ester derivant of the present invention has a carbon-carbon double bond and has a lamination crystal structure wherein molecules in two adjacent molecule planes are antiparallel.

The molecular plane refers to a plane formed by a carbon-carbon double bond of the molecules of the ester derivant. Further, to explain more specifically the structure in which molecules in two adjacent molecule planes are antiparallel, two adjacent molecular planes in the crystal structure of the ester derivant are oppositely stacked. That is, the one of two molecular planes adjacent in the lamination direction is the upper surface and the other is the rear surface when viewing from one side of the lamination direction.

The ester derivant is only required to be an ester derivant having a carbon-carbon double bond, but is preferably a dien containing an ester substituent, and more preferably a conjugate dien containing an ester substituent.

Further, it is preferable that ester derivant has at least two substituents, one of which is an ester substituent. The ester substituent is not particularly limited, and a suitable example may be one having a functional group of a hydrocarbon group, halogenated hydrocarbon group, amino group, or aminoalkyl group.

The conjugate dien having an ester substituent, one of an example of ester derivant, may be a muconic acid derivant or a sorbic acid derivant, for example.

More specifically, the ester derivant is preferably denoted by a general formula (2):

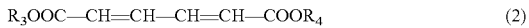

$$R_3OOC-CH=CH-CH=CH-COOR_4 \quad (2)$$

where $R_3$ and $R_4$ are hydrocarbon groups, each of which may have a functional group.

The $R_3$ and $R_4$ are only required to be a hydrocarbon group having a functional group other than a hydrocarbon group. A preferred example is a benzyl group containing ether bond. Particularly referable examples for the ether bond in the benzyl group are $CH_3O-$, $C_2H_5O-$, $C_3H_7O-$, $C_4H_9O-$, $C_6H_5O-$.

The ester derivant denoted by the foregoing general formula (2) preferably has a constant configuration at the portion of carbon-carbon double bond. Namely, the ester derivant of the general formula (2) is preferably a (Z, Z) form, or a (E, E) form. However, (E, Z) form may also be used.

In the foregoing structure, as described above, the ester derivant of the present invention forms a crystal in which the molecules alternately face upward or downward. Therefore, as described later, by proceeding polymerization reaction in such a crystal structure, a stereoregular polymer of disyndiotactic structure may be obtained. That is, the ester derivant is useful to create the stereoregular polymer.

Further, a production method of an ester derivant of the present invention comprises the step of forming a lamination crystal structure using a carboxylic acid having a carbon-carbon double bond and a compound having a functional group that can react to a carboxyl group of the carboxylic acid, so that molecules in two adjacent molecule planes are antiparallel.

The carboxylic acid is only required to be one having a carbon-carbon double bond; preferable example include a single base unsaturated carboxylic acid, such as sorbic acid, crotonic acid, or tiglic acid; and a dibasic unsaturated carboxylic acid, such as muconic acid, maleic acid, fumaric acid, citraconic acid, or mesaconic acid. A preferred is a muconic acid or a sorbic acid containing conjugate dien.

Further, the compound containing a functional group reacting to the carboxyl group is not limited, and is only required to be one allowing the hydrocarbon group having a functional group other than a hydrocarbon group to be incorporated in the carboxylic acid having dien. A possible example may be halogenated benzyl containing ether bond.

With this method, obtained is an ester derivant having a crystal structure in which the molecules in the adjacent molecular planes are antiparallel. Therefore, as described later, by proceeding polymerization reaction in such a crystal structure, a stereoregular polymer of disyndiotactic structure may be obtained.

Note that, the esterification in the foregoing method is not limited, and one of the conventional methods may be used; a possible example may be esterification with heating/dehydration in the presence of acid catalyst, or esterification with reaction of acid chloride and alcohol.

Further, apart from the conventional esterification, the foregoing process may be performed by reacting a carboxylic acid having a carbon-carbon double bond with a compound having a functional group that can react to a carboxyl group of the carboxylic acid dien, using hexamethylphospholamide as a solvent, in the presence of a potassium carbonate.

Particularly, by carrying out esterification with a solvent of hexamethylphospholamide and a catalyst of potassium carbonate, an ester derivant with specific stereoregularity can be obtained at a higher rate while suppressing isomerization of the product. Namely, the foregoing esterification carries out reaction with secure acquirement of an ester derivant having a specific configuration at a high selectivity.

Note that, the foregoing esterification method is not limited to the method of producing an ester derivant with a column structure in which the molecules of two adjacent molecular planes are aligned in antiparallel, like the one according to the present invention. The method will be suitably used for esterification of various carboxylic acid diens. Namely, the foregoing esterification method suppresses the isomerization in esterification reaction as much as possible, allowing high-rate acquisition.

Further, a production method of a stereoregular polymer of the present invention comprises the step of polymerizing a crystal of the ester derivant containing dien either by light irradiation or heating of the crystal.

This method carries out polymerization either by irradiation or by heating, while maintaining the ester derivant in a crystal state. Polymerization reaction in a crystal state ensures strong binding of molecule alignment in the crystal. Therefore, as with the ester derivant of the present invention, when the polymerization is performed to a crystal in which molecules in two adjacent molecule planes are antiparallel, it is possible to proceed polymerization reaction with a specific stereoregularity. Namely, by using an ester derivant having a controlled crystal structure formed by molecules, it is possible to obtain a stereoregular polymer of a disyndiotactic structure.

Note that, the light irradiation may be performed by visible light, ultraviolet light, X-ray or γ-ray; and ultraviolet light, X-ray or γ-ray are particularly preferable. With X-ray or γ-ray with high-permeability, reaction evenly occurs in the entire of the crystal, thus obtaining a crystal of a stereoregular polymer with significantly reduced deformation or defect.

BEST MODE FOR CARRYING OUT THE INVENTION

One embodiment of the present invention is described below with reference to FIGS. 1 and 2.

A. Structures of Stereoregular Polymer and the Monomer thereof

Figure 1:
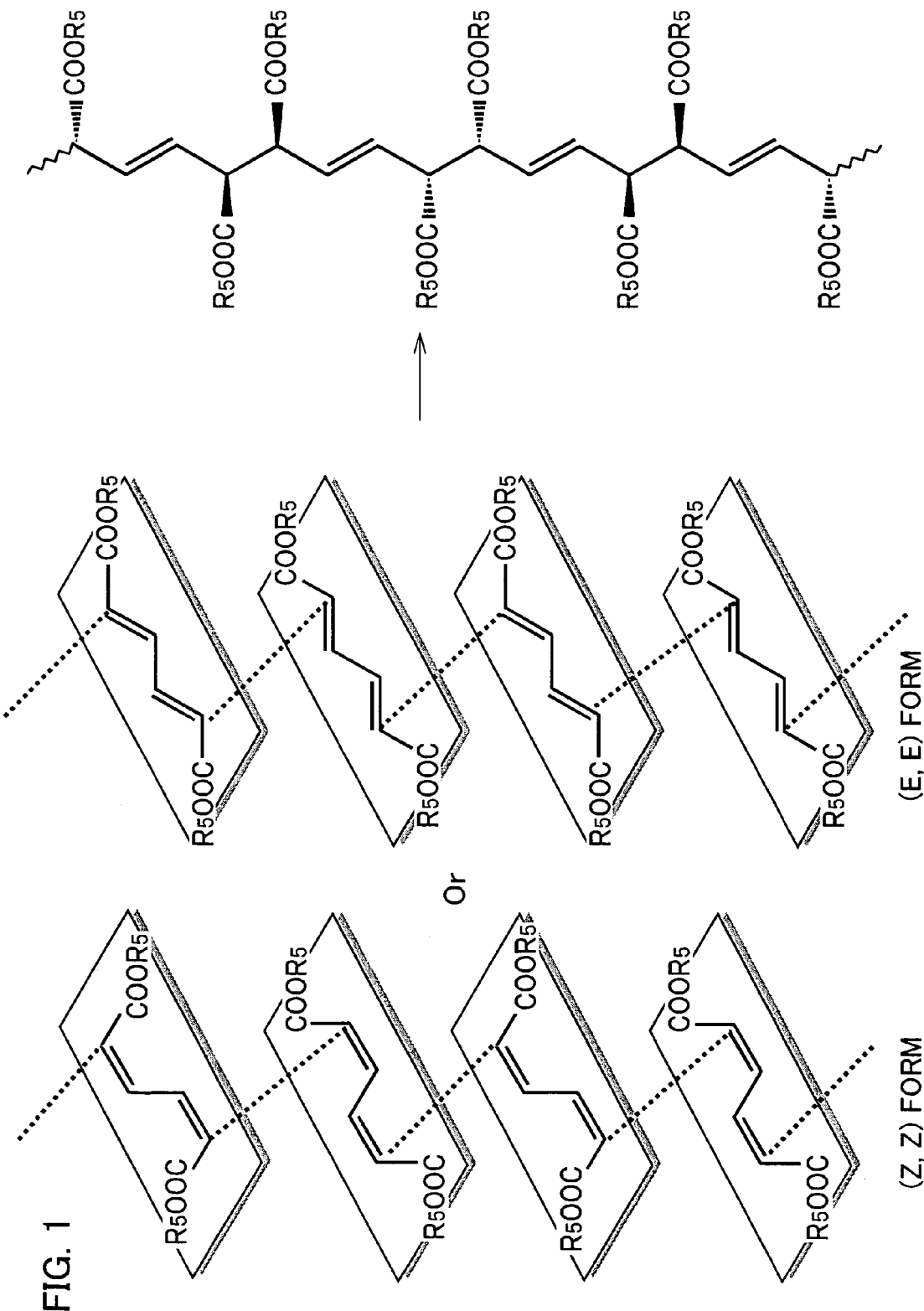
FIG. 1 is a drawing illustrating structures of a stereoregular polymer of the present invention and the monomer thereof.
Figure 2:
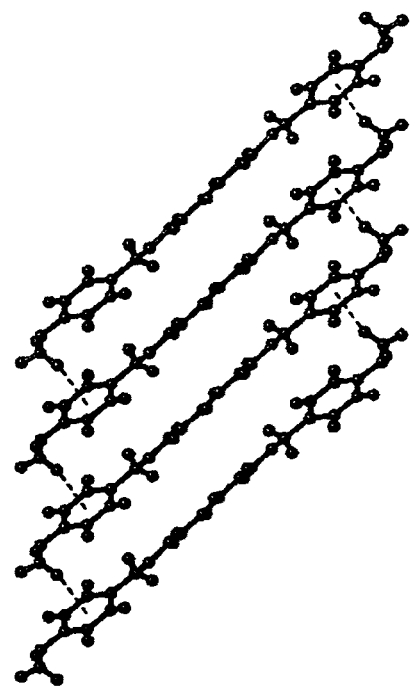
FIGS. 2(a) through 2(c) are drawings illustrating the structure of (Z, Z)-muconic acid di(4-methoxy benzyl) found by X-ray crystal structure analysis.
Figure 2:
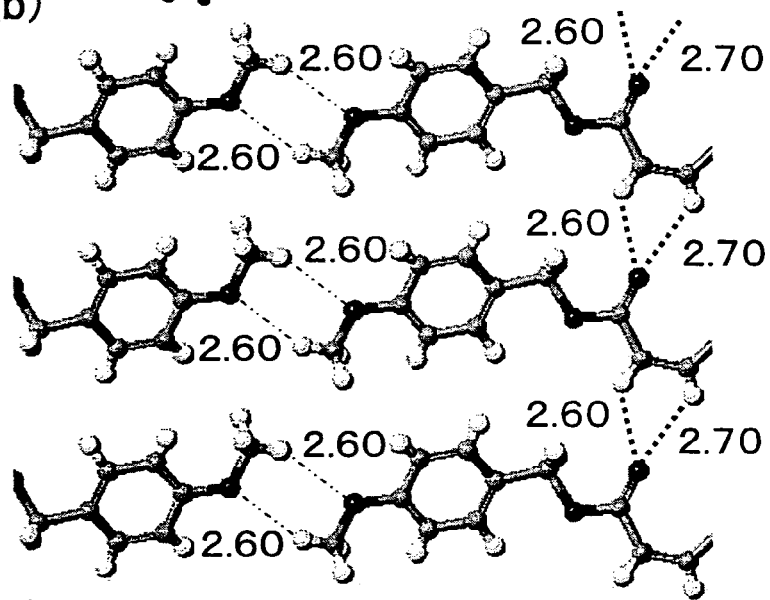
Figure 2:
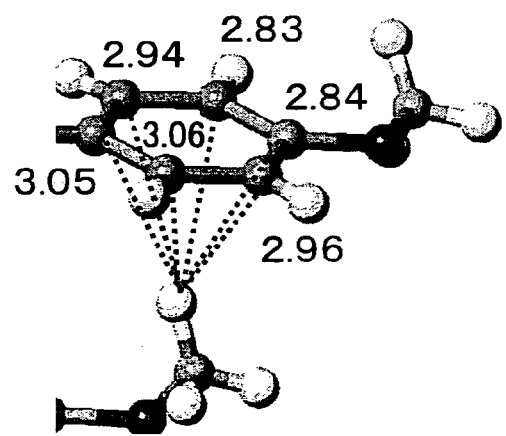

With reference to FIGS. 1 and 2, the following describes the structure of stereoregular polymer, and the structure of monomer constituting the stereoregular polymer, an ester derivant.

1) Structure of Stereoregular Polymer

The stereoregular polymer of the present invention, whose stereoregularity is disyndiotactic, contains at least one ester substituent.

The repeating units of the stereoregular polymer is preferably formed by subjecting muconic acid derivant to polymerization; that is, it is preferable that the repeating unit is one denoted by the foregoing general formula (1). Further, $R_1$ and $R_2$ of the general formula (1) express hydrocarbon groups, each of which may have a functional group, and are preferably a benzyl group having ether bond.

That is, the stereoregular polymer of the present invention is preferably has repeating units denoted by the following general formula (3),

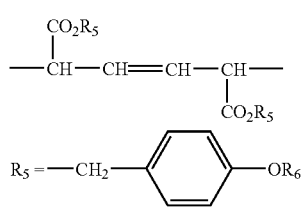

(3)

where $R_5$ expresses a benzyl group having ether bond, and $R_6$ expresses a hydrocarbon group. Further, it is more preferable that $R_6$ is a methyl group, that makes $R_5$ a methoxy benzyl group.

The following example uses the stereoregular polymer (hereinafter referred to as a muconic acid polymer) having the repeating units denoted by the general formula (3).

As shown after the arrow in FIG. 1, the stereoregularity of this muconic acid polymer is disyndiotactic. Specifically, in this muconic acid polymer, the configuration of two carbons (hereinafter referred to as a stereocenter) to which —$COOR_5$ are bonded in the repeating unit differs from that of the two stereocenters in an adjacent unit. The configurations of the stereocenters of the respective repeating units are alternately identical.

In other words, the muconic acid polymer has repeating units each denoted by the general formula (3), but there are two kinds of repeating unit with different configurations of stereocenter. These different units alternately appear with a certain cycle. Such a stereoregularity is called disyndiotactic.

1) Structure of Monomer

Next, the following explains a monomer (muconic acid monomer hereinafter) used to obtain the muconic acid polymer. As described above, the muconic acid polymer denoted by the general formula (3) is formed through polymerization of a muconic acid derivant. Therefore, the muconic acid monomer is preferably expressed by the following general formula (4),

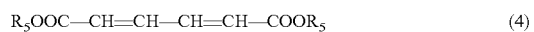

(4)

where $R_5$ expresses a benzyl group having ether bond.

The substituent (—$COOR_5$) contained in the muconic acid monomer denoted by the foregoing formula (4) is identical to the substituent contained in the muconic acid polymer denoted by the foregoing formula (3).

As shown before the arrow in FIG. 1, each muconic acid monomer of the general formula (4) has a molecular plane having a carbon-carbon double bond. The muconic acid monomer may be a (Z, Z) form in which both of the configurations of the carbon-carbon double bond are cis-constitution, a (E, E) form in which both of the configurations of the carbon-carbon double bond are trans-constitution, or a (E, Z) monomer in which one of the configurations of the carbon-carbon double bond is cis and the other is trans-constitution. Among these three isomers, the (Z, Z) form or the (E, E) form is preferred to obtain the muconic acid polymer. The use of (E, Z) polymer however still allows acquirement of the foregoing muconic acid polyrmer.

As shown in FIG. 1, a muconic acid monomer of the (Z, Z) form or the (E, E) form has a crystal of column structure in which the molecular planes are laminated. In this structure of crystal, the one of two molecular planes adjacent in the lamination direction is the upper surface and the other is the rear surface when viewing from one side of the lamination direction. Namely, the crystal of muconic acid monomer has a column structure in which the upper and rear molecular surfaces alternately appear in the lamination. In other words, the crystal of muconic acid monomer has a column structure in which the molecules are aligned so that the molecules in the two adjacent molecule planes are antiparallel. The crystal of the muconic acid monomer contains plural column structures that are aligned in the direction vertical to the lamination direction.

The reason why the crystal of muconic acid monomer has such a column structure may be thus assumed: there is weak intermolecular interaction between the adjacent muconic acid monomers within the column structure and between the column structures.

As a general sense, the molecular alignment of the crystal of monomer is greatly changed in the presence of strong intermolecular interaction, such as hydrogen bond or ionic bond. That is, a monomer forms a crystal by cooperation of the specific-hydrogen-bond orientation and the specific-ionic-bond intermolecular interaction.

Meanwhile, there is a theory that relatively weak intermolecular interaction than the hydrogen bond or ionic bond also functions as a factor for controlling the molecular alignment of the crystal. Examples of the weak intermolecular interaction include halogen-halogen interaction, π-π stacking, CH/O interaction, CH/N interaction, CH/π interaction, or the like. The halogen-halogen interaction is said to be caused by the anisotropy of the electron distribution on the halogen atom, and the π-π stacking is interaction among π electrons that is caused when the π planes of two aromatic rings are oppositely aligned. The CH/O interaction, and the CH/N interaction occur when the OH or NH, that relates to strong hydrogen bond such as OH/O or NH/H, is replaced with CH weaker in degree of acidity. Further, CH/π interaction occurs when the OH or N is replaced with a π electron weaker in basicity.

The inventors of the present invention have reported that the crystal of the monomer formed by the strong hydrogen bond, such as OH/O or NH/H, or by intermolecular force using halogen-halogen interaction tends to form a column structure in which the molecules are aligned in parallel.

On the other hand, the crystal of the muconic acid monomer is assumed to be formed by relatively weak intermolecular interaction, such as the CH/O interaction, the NH/N interaction, or the CH/π interaction, that occurs within the column structure and between the column structures. Therefore, in the crystal of the monomer formed by such a weak intermolecular interaction, such as the crystal of muconic acid monomer of the present invention, tends to have a column structure in which the molecules are aligned in antiparallel.

With reference to FIGS. 2(a) through 2(c), the following describes an example using the muconic acid monomer of the general formula (4) in which $R_5$ is a methoxy benzyl group.

In the column structure of the muconic acid monomer, it is assumed that the CH/O interaction and the CH/π interaction occur between the monomers adjacent in the column direction. As denoted by the broken line in 2(b), the CH/O interaction occurs between the hydrogen at the portion of the carbon-carbon double bond and the carbonyl oxygen of the carboxyl group. Further, as denoted by the chain double-dashed line in FIGS. 2(a) and 2(c), the CH/π interaction occurs between the methoxy group of the methoxy benzyl group and the benzene ring. In contrast, in the column structure, as shown in FIG. 2(b), the CH/O interaction occurs between the methoxy groups of the methoxy benzyl groups contained in the monomers adjacent in the direction vertical to the column direction.

As explained, the molecular alignment of the crystal of muconic acid monomer is controlled by the CH/O interaction and the CH/π interaction that occur within the column structure and between the column structures. Therefore, the crystal of muconic acid polymer has a structure in which the molecules in the two adjacent molecule planes are aligned in antiparallel in the column structure, while the column structure is aligned in the direction orthogonal to the lamination direction.

B. Production Methods of Stereoregular Polymer and the Monomer thereof

The following describes production methods of stereoregular polymer and the monomer thereof. Note that, as with the example above, the following example also uses the muconic acid polymer denoted by the foregoing general formula (3) as a stereoregular polymer, and the muconic acid monomer denoted by the foregoing general formula (4) as the monomer, and the respective production methods are described.

1) Production Method of Muconic Acid Polymer

The muconic acid polymer with the configuration explained in the A 1) above may be obtained through solid-phase polymerization, that clearly shows steleoselectivity and stereospecificity, allowing control of the structure of the product. Specifically, the muconic acid polymer may be obtained by subjecting the muconic acid monomer described in A 2) above to solid-phase polymerization.

Topochemical polymerization is preferably performed as the solid-phase polymerization. In the topochemical polymerization, a stereoregular polymer can be produced by proceeding polymerization reaction, with minimum movement of atoms or substituent without changing position of center of gravity of each monomer molecule, or symmetry of the crystal in polymerization reaction. The reaction path and reaction speed in topochemical polymerization depend on the crystal structure, that is an aggregation of monomer molecules, and the structure of the resultant polymer is determined depending on the molecular sequence of the crystal. Therefore, the topochemical polymerization allows acquirement of a polymer with desired structure by control of crystal structure of the monomer, thereby easily producing a polymer having specific stereo regularity.

More specifically, topochemical polymerization is caused in the muconic acid monomer (shown before the arrow in FIG. 1) having a crystal of a column structure by performing light irradiation using visible light, ultraviolet light, X-ray, γ-ray etc. or by heating the monomer. Through this polymerization, obtained is a muconic acid polymer. In other words, the muconic acid monomers are bonded at the position denoted by the broken lines shown in FIG. 1 through topochemical polymerization, thus producing a muconic acid polymer.

In topochemical polymerization with light irradiation, the light irradiation is preferably performed at room temperature for a time range from 10 minutes to 100 hours, more preferably for 1 hour to 10 hours. On the other hand, in topochemical polymerization by heating, the heating is preferably performed at 40° C. to 200° C., more preferably at 80° C. to 120° C. Further, the heating time may be decided according to heating temperature, but preferably in a range from 10 minutes to 200 hours, more preferably 1 hour to 20 hours. Further, the topochemical polymerization may be performed with both light irradiation and heating, so that the polymerization time is reduced.

Note that, to obtain the foregoing muconic acid polymer, it is preferable to use the crystal of (Z, Z) form or that of (E, E) form.

As explained, in topochemical polymerization, polymerization reaction is caused in a solid body by light irradiation or heating; therefore, other additives than monomer, such as reaction solvent, catalyst etc. is not required, and separation of the produced polymer is not necessary. Further, since all the monomer materials can be converted into polymers, it produces no wastes, thus reducing environmental burden.

2) Production Method of Muconic Acid Monomer

The muconic acid monomer explained in the A 2) above may be obtained by reacting of muconic acid and halogenide of methoxy benzyl so as to esterify the carboxyl group of muconic acid. A synthetic muconic acid monomer may be made of a (Z, Z) form muconic acid and a (E, E) form muconic acid. Since the (E, E) form of muconic acid is more thermodynamically stable then the (Z, Z) form muconic acid, the (Z, Z) form muconic acid is more preferable for the starting material.

The (Z, Z) form muconic acid, as the starting material, is reacted with halogenide of methoxy benzyl in the presence of potassium carbonate, using a hexamethylphosholamide (HMPA) as a solvent, thus producing a muconic acid monomer as a mixture of (Z, Z) form muconic acid and (E, Z) form muconic acid (Formula 5).

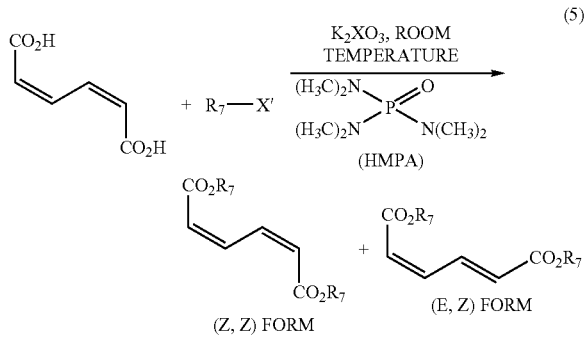

(5)

(Z, Z) FORM    (E, Z) FORM (R7 expresses methoxy benzyl group, and X' expresses halogen)

The (Z, Z) form and (E, Z) form are generally dividable by column chromatography. Thus, the (Z, Z) form muconic acid monomer and the (E, Z) form muconic acid monomer produced through the reaction of formula (5) can be obtained as separated monomers.

Further, a (E, E) form muconic acid monomer may be obtained by the reaction of the formula (5) as in the example above, that produces a muconic acid monomer as a mixture of (Z, Z) form and (E, Z) form. Then, by irradiating the (Z, Z) form muconic acid monomer and the (E, Z) form muconic acid monomer with ultraviolet light or other light, they are isomerized into the (E, E) form muconic acid monomer that is more thermodynamically stable. In this way, only a (E, E) form muconic acid monomer is obtained.

The amount of muconic acid and halogenide of methoxy benzyl used for the foregoing esterification reaction may be decided so that their amounts are equal in theoretical quantity. More specifically, it should be decided so that the number of the carboxyl group of the muconic acid and the methoxy benzyl group contained in the halogenide of the methoxy benzyl are equal. The amount of hexamethylphosholamide is not limited but should be enough to dissolve the muconic acid. Further, the potassium carbonate is preferably 0.5 to 10 times, more preferably 1 to 2 times the muconic acid in theoretical amount.

The foregoing method does not produce a mixture of (E, Z) form and (E, E) form, that is not easily separated by column chromatography; therefore, the method produces highly purified (Z, Z) form, (E, Z) form and (E, E) form. Further, if the method is performed with the same esterification as the formula (5), it is possible to obtain the (Z, Z) form muconic acid monomer as the main product.

The foregoing new method of esterificating carboxylic acid has been found by the inventors of the present invention. This esterification method differs from those conventionally performed, for example, esterification with heating/dehydration in the presence of acid catalyst, or esterification with reaction of acid chloride and alcohol.

In the foregoing conventional method, particularly in esterificating carboxylic acid diene; an esterification compound, the product of the reaction, is included in the isomer, that is a mixture of (Z, Z) form, (E, Z) form and (E, E) form, depending on the material and the reaction condition. However, in the foregoing conventional method, isomerization to the (E, Z) form and (E, E) form more easily occurs, and there is some difficulties to obtain (Z, Z) form at a high rate. Further, separation of (E, Z) form to/from (E, E) form is considered more difficult; therefore the resulting isomers are not obtained as separate monomers.

In contrast, as described above, with the use of a solvent of hexamethylphospholamide and a catalyst of potassium carbonate, esterification compound of (Z, Z) form can be obtained at a higher rate while suppressing isomerization into (E, Z) form or (E, E) form. Further, the resulting esterification compounds do not include a mixture of (E, Z) form and (E, E) form, thus easily obtaining the respective isomers. Namely, the esterification method of the present invention suppresses the isomerization as much as possible, allowing acquirement of esterification compound, thus obtaining an esterification compound with a specific configuration at a high rate.

Note that, the foregoing esterification method is not limited to the example described in the A 2) above, that produces a muconic acid monomer with a column structure in which the molecules of two adjacent molecular planes are aligned in antiparallel. As described later in Examples, the method will be suitably used for obtaining various esterification compounds. Namely, the foregoing esterification method can be widely used as a method of suppressing the isomerization in esterification reaction as much as possible, allowing high-rate acquirement of an esterification compound with a specific configuration.

The concrete Examples of the present invention are described below with reference to FIGS. 2 or 9. [Measurements of fusing point, thermolysis temperature and spectrum]Fusing point and thermolysis temperature were measured in the nitrogen stream at a temperature-raising speed=10° C./min., by performing thermogravimetry and differential thermal analysis using a device for simultaneous measurement of thermogravimetry/differential (TG/DTA6000, product of Seiko Instruments Inc.). According to the results of measurement, the fusing point and thermolysis temperature were found.

$^1$H-NMR spectrum was measured using JMN A-400 (product of JEOL: 400MHz) with a solvent of $CDCl_3$. Similarly, $^{13}$C-NMR spectrum was measured using JMN A-400 (product of NIHON DENSI: 400 MHz) with a solvent of $CDCl_3$.

Ultraviolet absorption spectrum was measured using an ultraviolet visible spectrophotometer (V-550, product of JASCO) with a solvent of acetonitrile.

Infrared absorption spectrum was measured using a Herschel FT-IR-430 (JACSO).

Profiling of powder X-ray diffraction spectrum was carried out using RINT-2100 (RIGAKU) with monochromic CuL irradiation ($\lambda$=1.5418 Å).

[X-ray Crystal Structure Analysis]

X-ray crystal structure analysis was performed by a Mo—Kα irradiation (1=0.71073 Å) monochromated by graphite, using a R-AXIS RAPID Imaging Plate diffractometer. The structure was analyzed by a direct method using SIR92 program, and was determined by a least-squares method. All calculations here were performed with crystal analysis software "Crystal Structure" (Molecular Structure Corporation).

EXAMPLE 1

(Z, Z)-muconic acid di(4-methoxy benzyl) and (E, Z)—muconic acid di(4-methoxy benzyl) were obtained as follows.

2.08 g (14.5 mmoL) (Z, Z)-muconic acid (product of Mitsubishi Chemical) and 20 ml hexamethylphospholamide (product of Tokyo Kasei) were mixed in a 100 mL eggplant-shaped flask; then a calcium chloride tube is attached to the eggplant-shaped flask, and the liquid was stirred until the (Z, Z)-muconic acid dissolved, thus creating a hexamethylphospholamide solution. Then, 5.05 g (36.6 mmol) potassium carbonate (product of Wako Pure Chemical) and 6.06 g (42.1 mmol) 4-methoxy benzyl chloride were added to the solution and the mixture was stirred for three days to cause reaction of the substances, thus obtaining a reaction mixture.

Next, 200 ml water was added to the reaction mixture, followed by two times extraction with 100 ml chloroform. The extraction liquid was cleaned by water and saturated salt water. Then, the resulting liquid was dried by sodium sulfate, and the chloroform was removed under low pressure, thus obtaining a yellow liquid. Further, methanol and water were added to the yellow liquid, and the separated white solid body was filtered and the resulting solid was dried under low pressure at a room temperature. The dried white solid body was subjected to column chromatography (Wako Gel C-200, chloroform), and the solvent was taken from the first liquid, followed by further drying, thus obtaining 3.02 g (yield=54%) (Z, Z)-muconic acid di(4-methoxy benzyl). Further, 0.71 g (yield=24%) (E, Z)—muconic acid di(4-methoxy benzyl) was obtained from the second liquid.

The fusion point and spectrum data of the obtained (Z, Z)—muconic acid di(4-methoxy benzyl) and (E, Z)-muconic acid di(4-methoxy benzyl) are shown in Tables 1 through 6.

TABLE 1

FUSION POINT OF MUCONIC ACID DI (4-METHOXY BENZYL)

| CONFIGURATION | FUSING POINT/° C.(CHCl$_3$) |
|---|---|
| (Z, Z)FORM | 82.9-83.2 |
| (E, E)FORM | 119.8-121.8 |
| (E, Z)FORM | 83.8-84.8 |

TABLE 2

CHEMICAL SHIFT OF PEAK OF $^1$H-NMR SPECTRUM OF MUCONIC ACID DI (4-METHOXY BENZYL)

| | | CONFIGURATION | |
|---|---|---|---|
| | | (Z, Z) FORM CHEMICAL SHIFT | (E, E) FORM CHEMICAL SHIFT |
| ATTRIBUTION POSITION OF H | NUMBER OF H | δ/ppm | δ/ppm |
| —C$H$=CHCO$_2$R | 2H | 7.91(m) | 7.28-7.34(m) |
| —C$_6$$H_4$ | 4H | 7.30-7.35(m) | |
| | 4H | 6.88-6.93(m) | 6.92-6.88(m) |
| —CH=C$H$CO$_2$R | 2H | 6.00(m) | 6.20(m) |
| —C$H_2$ | 4H | 5.13(s) | 5.14(s) |
| —OC$H_3$ | 6H | 3.82(s) | 3.81(s) |

TABLE 3

CHEMICAL SHIFT OF PEAK OF $^{13}$C-NMR SPECTRUM OF MUCONIC ACID DI (4-METHOXY BENZYL)

| | CONFIGURATION | |
|---|---|---|
| | (Z, Z) FORM CHEMICAL SHIFT | (E, E) FORM CHEMICAL SHIFT |
| ATTRIBUTION POSITION OF C | δ/ppm | δ/ppm |
| —$C$=O | 165.48 | 165.76 |
| —$C_6$H$_4$ | 159.70 | 159.77 |

TABLE 3-continued

CHEMICAL SHIFT OF PEAK OF $^{13}$C-NMR SPECTRUM OF MUCONIC ACID DI (4-METHOXY BENZYL)

| | CONFIGURATION | |
|---|---|---|
| | (Z, Z) FORM CHEMICAL SHIFT | (E, E) FORM CHEMICAL SHIFT |
| ATTRIBUTION POSITION OF C | δ/ppm | δ/ppm |
| —$C$H= | 138.21 | 141.08 |
| —$C_6$H$_4$ | 130.18 | 130.27 |
| | 127.80 | 128.31 |
| | 124.11 | 127.70 |
| —$C$H= | 114.00 | 114.00 |
| —$C$H$_2$ | 66.13 | 65.56 |
| —O$C$H$_3$ | 55.30 | 55.30 |

TABLE 4

ABSORPTION PEAK OF ULTRAVIOLET ABSORPTION SPECTRUM OF MUCONIC ACID DI (4-METHOXY BENZYL)

| CONFIGURATION | ABSORPTION MAXIMUM WAVELENGTH $\lambda_{max}$(nm) | MOL ABSORBANCE COEFFICIENT $\epsilon$(mol$^{-1}$dm$^3$cm$^{-1}$) |
|---|---|---|
| (Z, Z)FORM | 227 | 23000 |
| (E, E)FORM | 263 | 28000 |
| (E, Z)FORM | 266 | 27100 |

TABLE 5

CHEMICAL SHIFT OF PEAK OF $^1$H-NMR SPECTRUM OF MUCONIC ACID DI (4-METHOXY BENZYL)

| ATTRIBUTION POSITION OF H | NUMBER OF H | CHEMICAL SHIFT δ/ppm | SPIN COUPLING CONSTANT J/Hz |
|---|---|---|---|
| trans-C$H$=CHCO$_2$R | 1H | 8.43 | 15.6, 11.6(dd) |
| —C$_6$$H_4$ | 4H | 7.20-7.35 | —(m) |
| | 4H | 6.87-6.91 | —(m) |
| cis-CH=C$H$CO$_2$R | 1H | 6.62 | 11.6(t) |
| trans-CH=C$H$CO$_2$R | 1H | 6.11 | 15.6(d) |
| cis-CH=C$H$CO$_2$R | 1H | 5.96 | 11.6(d) |
| —C$H_2$ | 2H | 5.16 | —(s) |
| | 2H | 5.14 | —(s) |
| —OC$H_3$ | 6H | 3.81 | —(s) |

TABLE 6

CHEMICAL SHIFT OF PEAK OF $^{13}$C-NMR SPECTRUM OF MUCONIC ACID DI (4-METHOXY BENZYL)

| ATTRIBUTION POSITION OF C | CHEMICAL SHIFT δ/ppm | |
|---|---|---|
| —$C$=O | 165.91 | 165.07 |
| —$C_6$H$_4$ | 159.67 | |
| —$C$H= | 140.78 | 138.82 |
| —$C_6$H$_4$ | 130.28 | 130.19 |
| | 128.97 | 127.97 |
| | 127.75 | 124.54 |
| —$C$H= | 114.00 | 113.96 |
| —$C$H$_2$ | 66.26 | 63.34 |
| —O$C$H$_3$ | 55.30 | |

Note that, in Tables 2 and 5, s, d, t and m indicate spectrum peaks in single line, double line, triple line and multiple line, respectively.

Further, to confirm the crystal structure, X-ray crystal structure analysis was carried out. FIGS. 2(a) through 2(c), FIGS. 3(a), 3(b) and FIG. 4 show the results for (Z, Z)—muconic acid di(4-methoxy benzyl).

Figure 3:
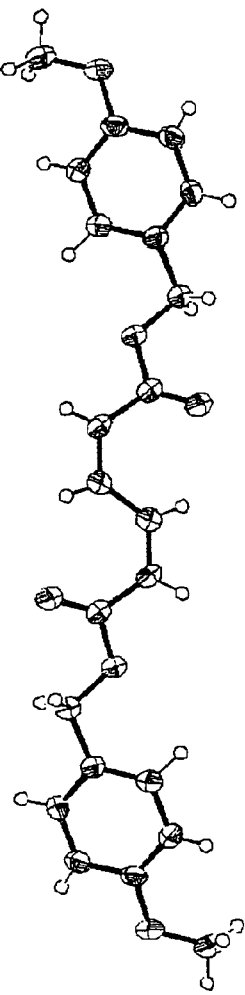
FIGS. 3(a) and 3(b) are drawings illustrating X-ray crystal structure analysis of (Z, Z)-muconic acid di(4-methoxy benzyl).
Figure 4:
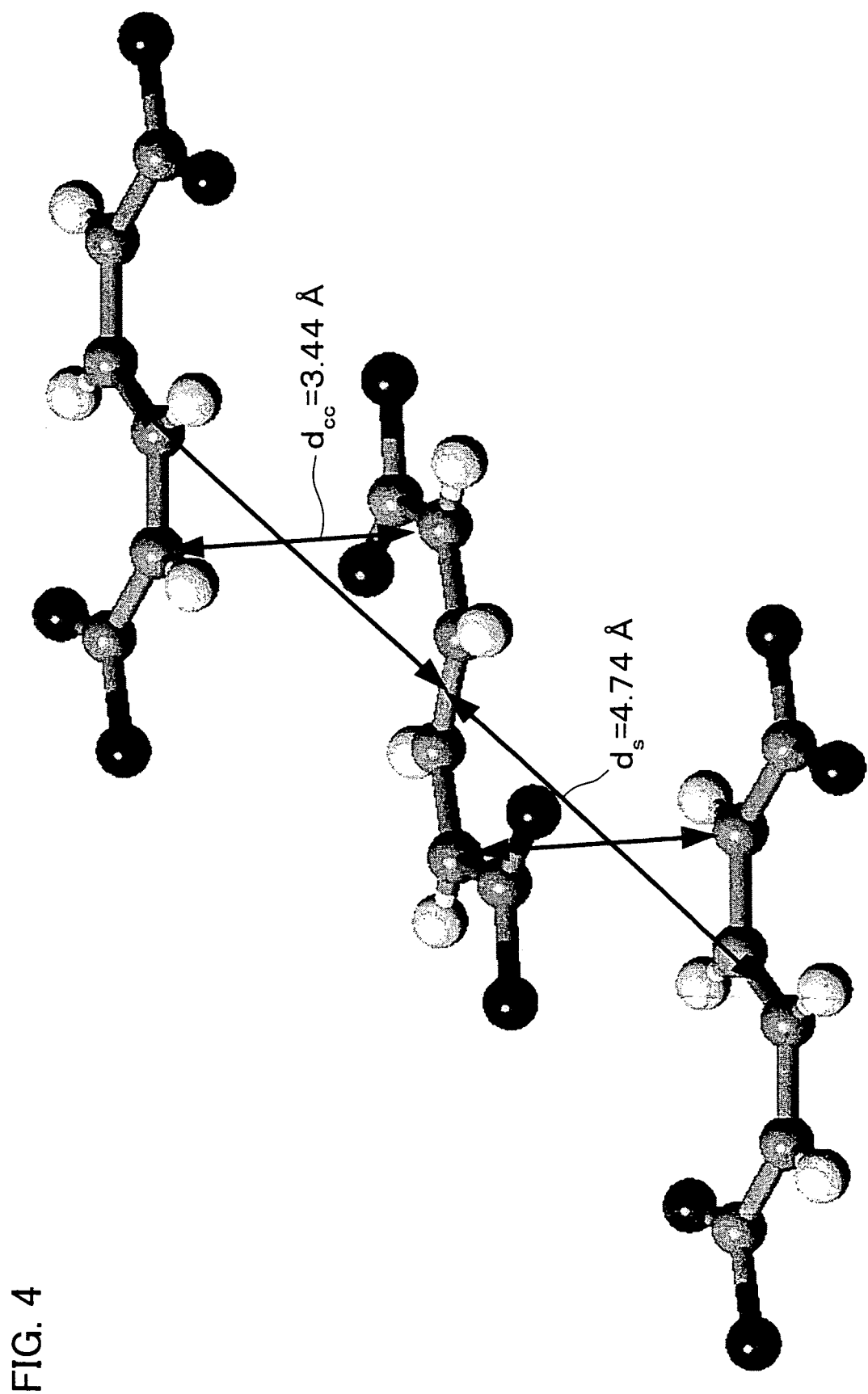
FIG. 4 is a drawing showing a lamination of (Z, Z)—muconic acid di(4-methoxy benzyl).

These results of X-ray crystal structure analysis showed that the resulting product was (Z, Z)-muconic acid di(4-methoxy benzyl) (FIGS. 3(a), 3(b)) with the column structure illustrated in FIG. 2(a). Further, as shown in FIG. 4, the distance (expressed as $d_s$ in the figure) between barycenters of the stacked molecules was 4.74 Å, and the distance (expressed as $d_{cc}$ in the figure) between carbons of the stacked molecules was 3.44 Å.

Further, as denoted by the broken line in FIG. 2(b), the distance between (i) the hydrogen at the portion of carbon-carbon double bond between the molecules in the column direction, and (ii) carbonyl oxygen of the carboxyl group was estimated at 2.60 Å to 2.70 Å (see the values in the figure). Therefore, it is assumed that there exists intermolecular CH/O interaction in this site in the column structure. Further, as denoted by the broken line in FIG. 2(c), the distance between the methoxy group of methoxy benzyl group and the benzene ring was estimated at 2.83 Å to 3.06 Å (see the values in the figure). Accordingly, it is assumed that there exists intermolecular CH/π interaction in this site in the column structure.

In contrast, as denoted by the chain double-dashed line in FIG. 2(b), the distance between each methoxy group of the molecules orthogonally positioned in the column direction was estimated at 2.60 Å (see the values in the figure). Accordingly, it is assumed that there exists intermolecular CH/O interaction in this site between the column structures.

EXAMPLE 2

(E, E)-muconic acid di(4-methoxy benzyl) was obtained as follows 3.00 g (21.1 mmoL) (Z, Z)-muconic acid and 30 ml hexamethylphospholamide were mixed in a 100 mL eggplant-shaped flask; then a calcium chloride tube is attached to the eggplant-shaped flask, and the liquid was stirred until the (Z, Z)-muconic acid dissolved, thus creating a hexamethylphospholamide solution. Then, 4.38 g (31.7 mmol) potassium carbonate and 6.61 g (42.2 mmol) 4-methoxy benzyl chloride were added to the solution and the mixture was stirred for three days to cause reaction of the substances, thus obtaining a reaction mixture.

Next, 300 ml water was added to the reaction mixture, followed by two times extraction with 150 ml chloroform. The extraction liquid was cleaned by water and saturated salt water. Then, the resulting liquid was dried by sodium sulfate, and a spatula of iodine was added thereto before subjected to ultraviolet irradiation for 6 hours using a high-pressure mercury lamp (SHL-100-2, 100 W, Pyrel filter; product of Toshiba). After the irradiation, chloroform was removed under low pressure, thus obtaining a yellow liquid. Further, methanol and water were added to the yellow liquid, and the separated white solid body was filtered and the solid was dried under low pressure at a room temperature, thus obtaining 5.78 g (yield=72%) (E, E)-muconic acid di(4-methoxy benzyl).

The fusion point and spectrum data of the obtained (E, E)—muconic acid di(4-methoxy benzyl) are shown in Tables 1 through 4.

Note that, in Table 2, s and m indicate spectrum peaks in single line and multiple line, respectively.

Figure 5:
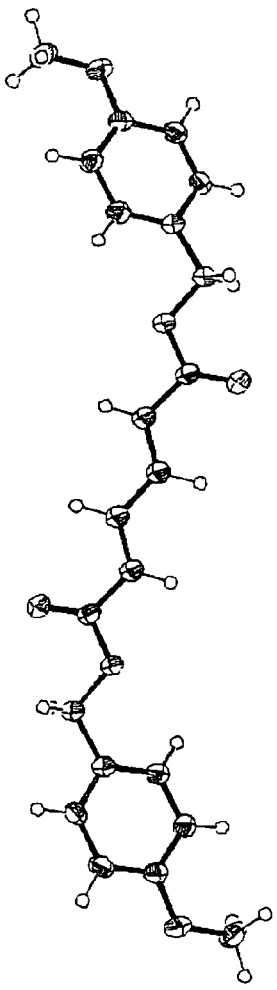
FIGS. 5(a) and 5(b) are drawings illustrating X-ray crystal structure analysis of (E, E)-muconic acid di(4-methoxy benzyl).
Figure 6:
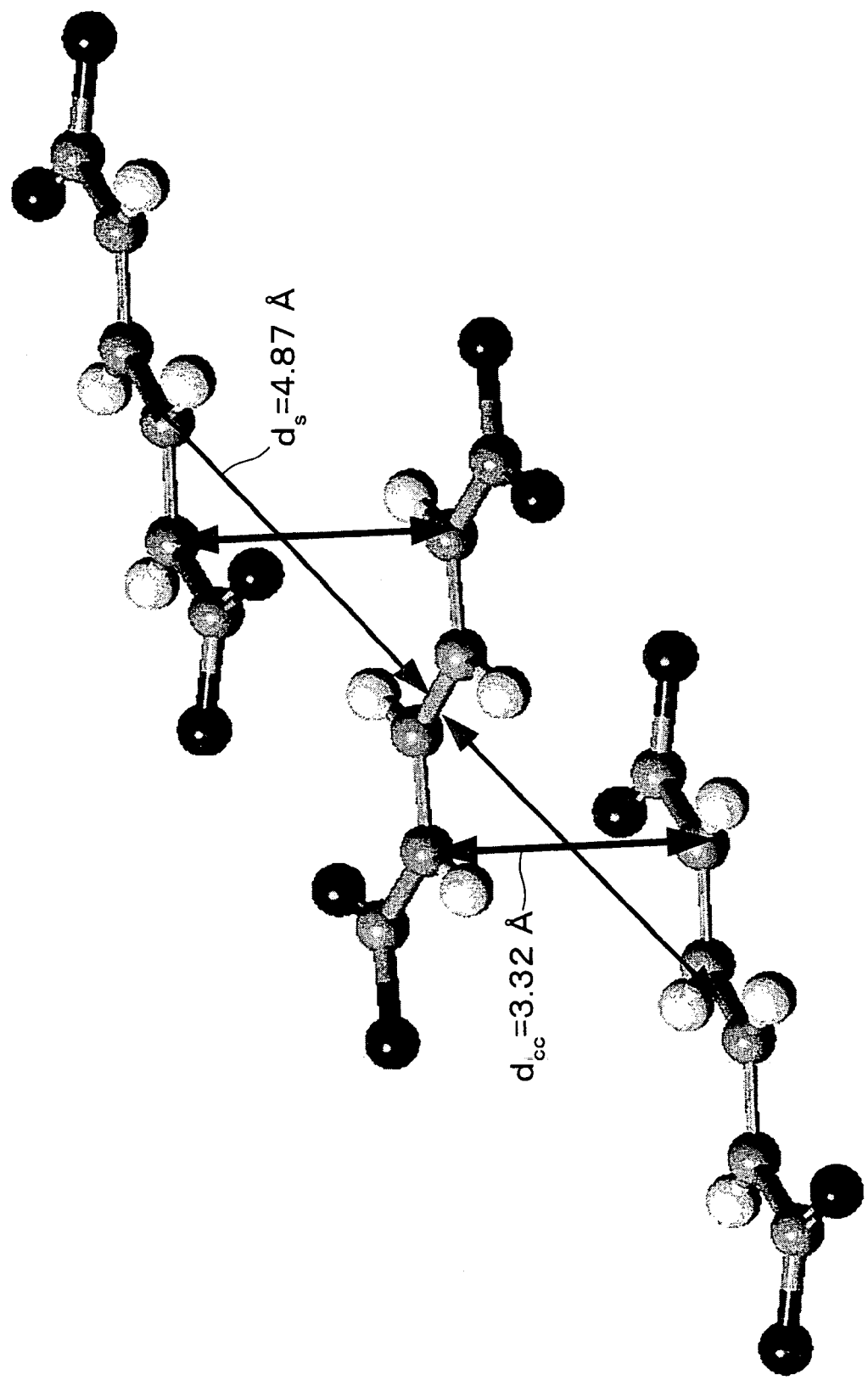
FIG. 6 is a drawing showing a lamination of (E, E)—muconic acid di(4-methoxy benzyl).

Further, to confirm the crystal structure, X-ray crystal structure analysis was carried out. FIGS. 5(a) through 5(b), and FIG. 6 show the results for (E, E)-muconic acid di(4-methoxy benzyl). These results of X-ray crystal structure analysis showed that the resulting product was (E, E)-muconic acid di(4-methoxy benzyl) (FIGS. 5(a), 5(b)) with the column structure. Further, as shown in FIG. 6, the distance (expressed as $d_s$ in the figure) between barycenters of the stacked molecules was 4.87 Å, and the distance (expressed as $d_{cc}$ in the figure) between carbons of the stacked molecules was 3.32 Å.

EXAMPLE 3

The same reaction as that of Example 1 was carried out; however, instead of 4-methoxybenzylchloride, 4-chrolobenzylbromide, 4-bromobenzylbromide, and 2,3,4,5, 6-pentafluorobenzylbromide were used in the same theoretical amount.

Table 7 shows the production amount of (Z, Z) form and (E, E) form of the obtained product. The reaction time is shown in the table.

TABLE 7

| REACTANT | REACTION TIME (day) | YIELD (%) | RATIO BETWEEN ISOMERS (Z,Z):(E,Z) |
|---|---|---|---|
| Cl—⟨C₆H₄⟩—CH₂Br | 2 | 96 | ~100:0 |
| Br—⟨C₆H₄⟩—CH₂Br | 2 | 82 | 99:1 |
| F₅—⟨C₆⟩—CH₂Br | 1 | 89 | ~100:0 |
| Br—⟨C₆H₄⟩—CH₂Cl | 3 | 78 | 70:30 |

As shown in Table 7, an esterified product was obtained with a high yield. Further, it can also be seen that a mixture of (Z, Z) form and (E, Z) form was obtained in all of the respective cases using halogenides with different benzyl groups. Further, in the product, (Z, Z) form is greater in amount than (E, Z) form in all cases.

Comparative Example

Esterification was carried out with a phase-transition catalyst. More specifically, as shown in the formula (6), muconic acid was reacted with 4-bromobenzylbromide with different bases and solvents (shown in Table 8) in the presence of potassium hydrogen tetra n-butylammonium.

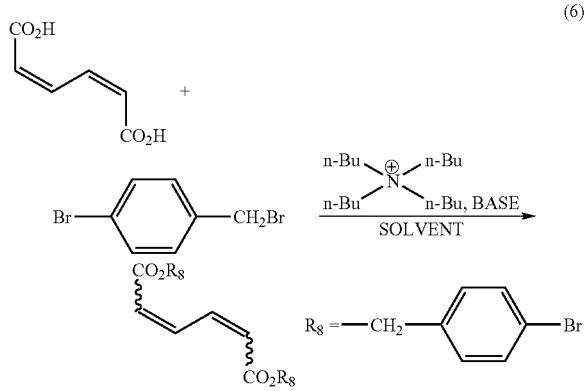

(6)

Reaction time, reaction condition, theoretical ratio between base/muconic acid, and ratio between isomers of the product is shown in Table 8. Note that, the respective isomers were determined by H-NMR spectrum measurement.

TABLE 8

| SOLVENT<br>BASE | H$_2$O/<br>CH$_2$Cl$_2$<br>KOH | H$_2$O/<br>C$_2$H$_4$Cl$_2$<br>KOH | H$_2$O/<br>C$_2$H$_4$Cl$_2$<br>K$_2$CO$_3$ | H$_2$O/<br>C$_2$H$_4$Cl$_2$<br>KOH |
|---|---|---|---|---|
| THEORETICAL RATIO (BASE/ MUCONIC ACID) | 4.4 | 4.4 | 2.2 | 2.0 |
| REACTION TEMPERATURE | REFLUX | ROOM TEMPERATURE | ROOM TEMPERATURE | ROOM TEMPERATURE |
| REACTION TIME | 1 HOUR | 3 DAYS | 3 DAYS | 3 DAYS |
| PRODUCT (%) | | | | |
| (Z, Z)FORM | 17 | 25 | 45 | 1.2 |
| (E, Z)FORM | 40 | 58 | 10 | 11 |
| (E, E)FORM | — | — | — | — |

As shown in Table 8, (Z, Z) form product and (E, Z) product were obtained, but no (E, E) product. Further, it can also be seen that the production amounts of (Z, Z) form and (E, Z) form depend on the reaction condition.

Figure 7:
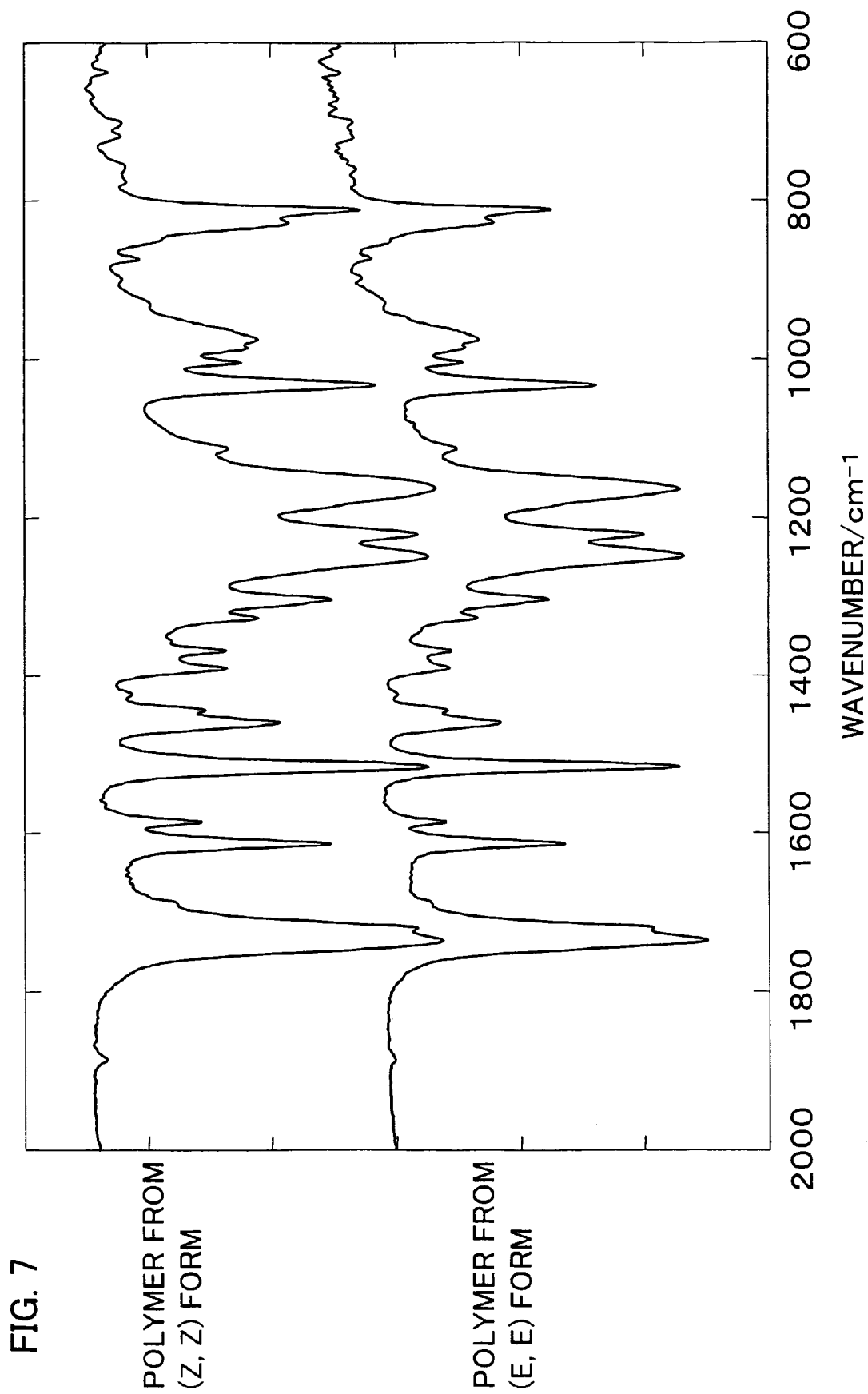
FIG. 7 shows infrared absorption spectrum of polymuconic acid di(4-methoxy benzyl) obtained by the (Z, Z)—muconic acid di(4-methoxy benzyl) and (E, E)-muconic acid di(4-methoxy benzyl).
Figure 8:
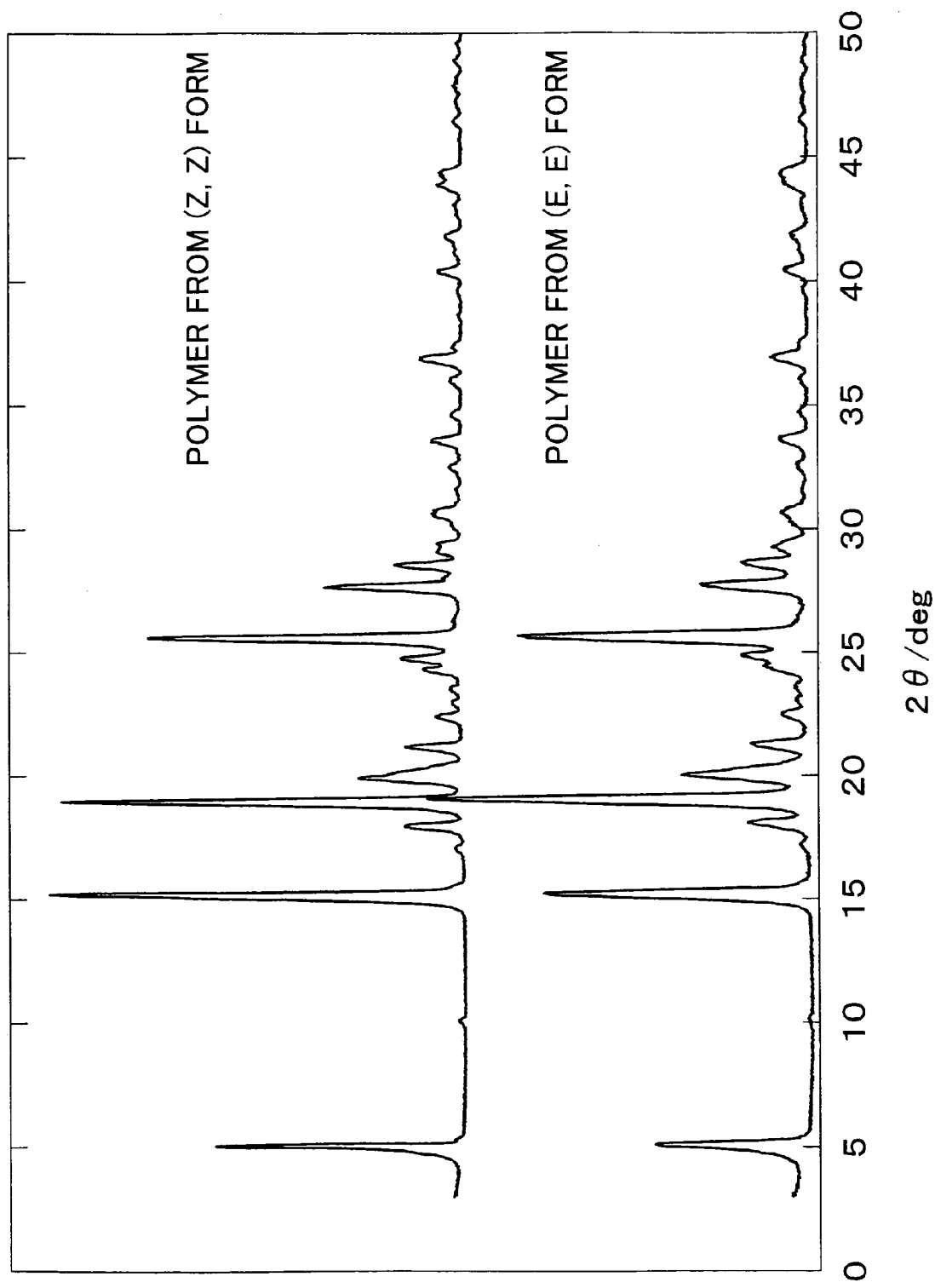
FIG. 8 shows powder X-ray diffraction spectrum of polymuconic acid di(4-methoxy benzyl) obtained by the (Z, Z)—muconic acid di(4-methoxy benzyl) and (E, E)-muconic acid di(4-methoxy benzyl).

As shown in FIGS. 7 and 8, the (Z, Z) form and the (E,Z) form were obtained in both Example 3 and the present comparative example. However, in Example 3, the products were mostly (Z, Z) forms, while the present comparative example did not result in production of a particular isomer with high yield.

EXAMPLE 4

A polymuconic acid di(4-methoxy benzyl) was obtained from (Z, Z)-muconic acid di(4-methoxy benzyl) and (E, E)—muconic acid di(4-methoxy benzyl) produced in Examples 1 and 2.

Specifically, a 31 mg (0.081 mmol) crystal of (Z, Z)—muconic acid di(4-methoxy benzyl) was placed in a dish and was irradiated with ultraviolet light for 8 hours at a room temperature. A high-pressure mercury lamp was placed at a 10 cm distance from the dish. Then, 50 ml chloroform was added to the obtained solid-body, stirred for an hour, and the not-dissolved part was taken out by filtration, thus obtaining 29 mg (yield=93%) white powder of polymuconic acid di(4-methoxy benzyl). This polymuconic acid di (4-methoxy benzyl) is hereinafter referred to as a polymer from (Z, Z) form. The same process as above was performed again with a 110 mg (0.31 mmol) crystal of (E, E)-muconic acid di(4-methoxy benzyl) was placed in a dish and was irradiated with ultraviolet light for 8 hours at a room temperature. Obtained is 96 mg (yield=81%) white powder of polymuconic acid di(4-methoxy benzyl).

Then the obtained polymer from (Z, Z) form and the polymer from (E, E) form were checked for thermal characteristic, and solubility to a solvent. The fusion point was 205° C. and the kick-off temperature was 270° C. These results have proved the superior thermotolerancy of the polymers.

Further, chloroform, 1,2-dichloroethane, o-dichlobenzene, toluen, dimethylformamide, dimethylsulfoxide, tetrahydrofuran, hexamethylphospholamide, trifluoroacetic acid, polar solvent of hexafluoro isopropanol, and fluorocarbon solvent. These results have proved the superior solvent resistance of the polymers.

Further, to compare a disyndiotactic polymer with a isotactic polymer in solvent resistance, a disyndiotactic polymer obtained from (E, E)-muconic acid di(4-methoxy benzyl) and a isotactic polymer obtained from (E, E)-muconic acid di(3-methoxy benzyl) were checked for solubility to organic solvents or acids. The results are shown in Table 9. As can be seen is the table, the isotactic polymer was insoluble to organic solvents, but soluble to strong sulfuric acid or trifluoroacetic acid. In contrast, the disyndiotactic polymer was insoluble not only to organic solvents but also to strong sulfuric acid or trifluoroacetic acid. Accordingly, disyndiotactic polymer is superior in solvent resistance.

TABLE 9

| SOLVENT | DISYNDIOTACTIC POLYMER OBTAINED BY (Z, Z) - muconic acid di (4-methoxy benzyl) | POLYMER OBTAINED BY (Z, Z) - 3 muconic acid di (4-methoxy benzyl) |
|---|---|---|
| DIMETHYL-FORMAMIDE | INSOLUBLE | INSOLUBLE |
| DIMETHYL-SULFOXIDE | INSOLUBLE | INSOLUBLE |
| HEXAMETHYL-PHOSPHOL-AMIDE | INSOLUBLE | INSOLUBLE |
| O-DICHLORO-BENZENE | INSOLUBLE | INSOLUBLE |
| CHLOROFORM | INSOLUBLE | INSOLUBLE |
| TETRA-HYDROFURAN | INSOLUBLE | INSOLUBLE |
| TRIFLUORO-ACETIC ACID | INSOLUBLE | INSOLUBLE |
| CONCENTRATED SULFURIC ACID | INSOLUBLE | INSOLUBLE |

Further, to check the configuration of the obtained polymer, infrared absorption spectrum, powder X-ray diffraction spectrum were measured. The results are shown in FIGS. 7 and 8.

Further, for X-ray crystal structure analysis, a monocrystal polymuconic acid di(4-methoxy benzyl) was obtained as follows.

More specifically, the 50 mg monocrystal of (Z, Z)—muconic acid di(4-methoxy benzyl) was degassed and sealed in Pyrex glass seal pipe, and was irradiated with γ ray (200 kGy) using cobalt 60 at a room temperature. Obtained was a polymer monocrystal of (Z, Z)-muconic acid di(4-methoxy benzyl).

Change in reaction with time was observed by infrared absorption spectrum measurement and powder X-ray diffraction spectrum measurement, and found that the reaction proceeds quantitatively. Further, one with good quality was picked from the obtained polymer monocrystals for X-ray crystal structure analysis. The result is shown in FIGS. 9(a) and 9(b).

Figure 9:
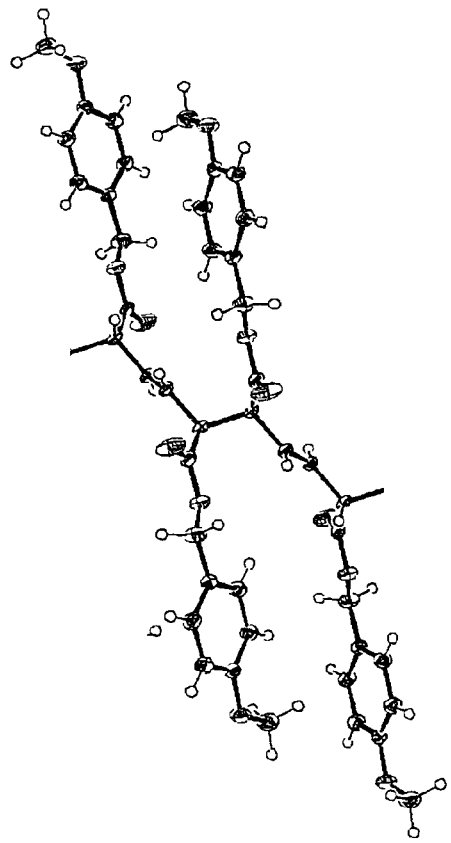
FIG. 9(a) and 9(b) are drawings illustrating X-ray crystal structure analysis of (Z, Z)-polymuconic acid di(4-methoxy benzyl).

As shown in FIGS. 7 through 9, the obtained polymer has a significantly high stereoregularity and high crystalline property. Further, it also shows that the configuration of polymers at the carbon-carbon double bond is trans, and that the polymers were formed through topochemical polymerization, that was reaction between the crystal layers. Further, it also shows that the stereoregularity of the obtained polymers are disyndiotactic.

Figure 10:
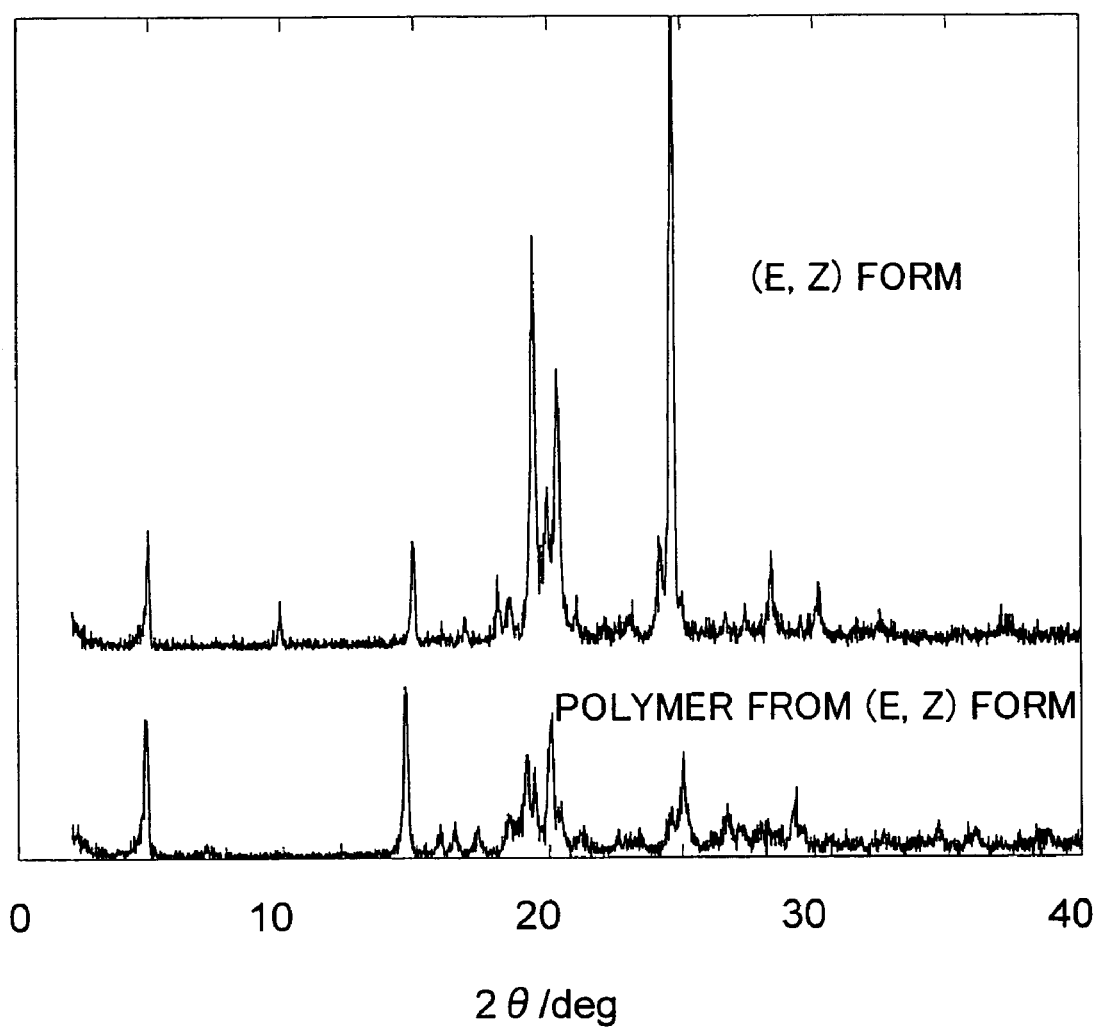
FIG. 10 shows powder X-ray diffraction spectrum of polymuconic acid obtained by the (E, Z)-muconic acid (4-methoxy benzyl) and polymuconic acid (4-methoxy benzyl) obtained therefrom.
Figure 11:
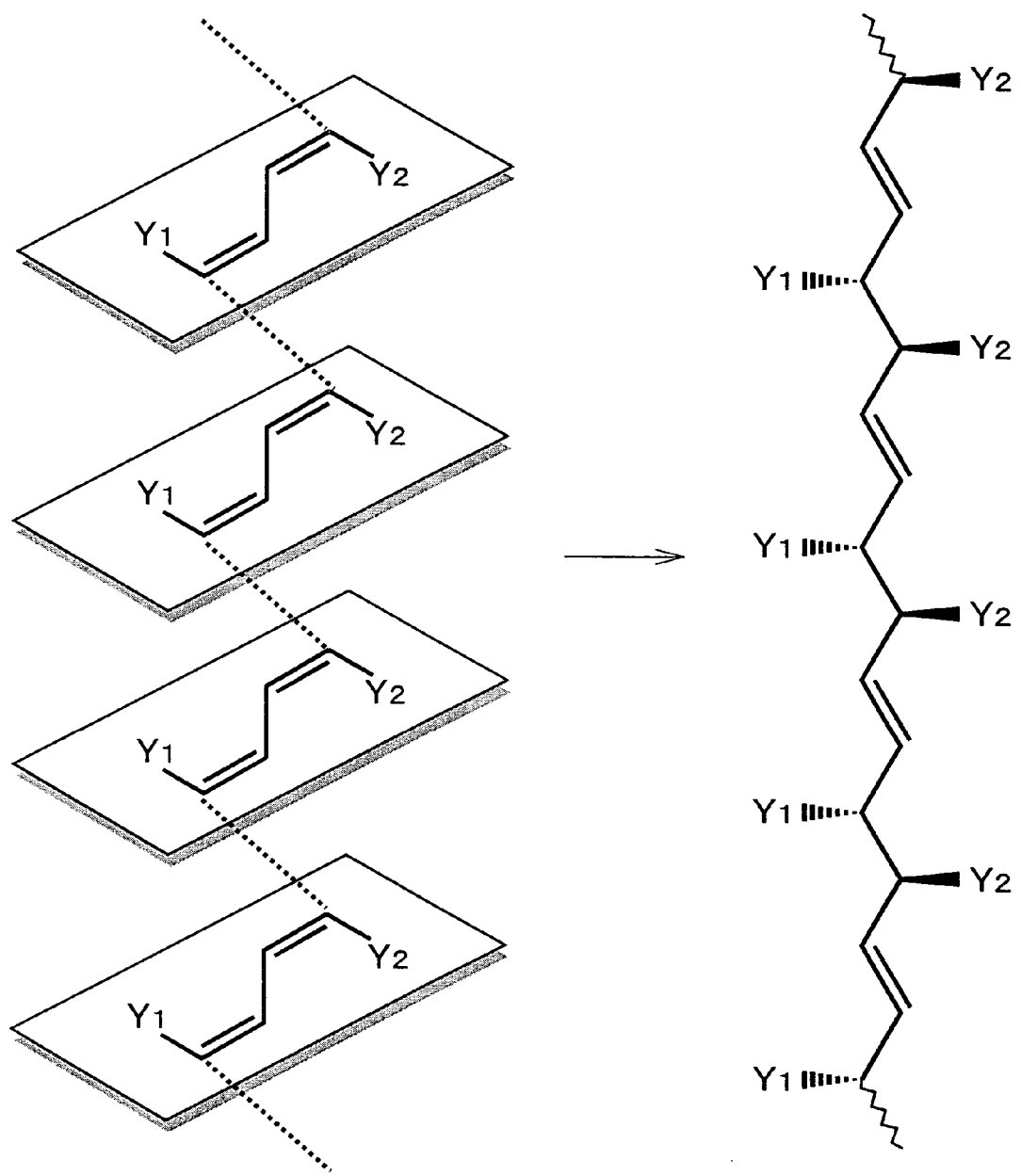
FIG. 11 is a conceptual diagram illustrating structures of a stereoregular polymer of a diisotactic structure and the monomer thereof.
Figure 12:
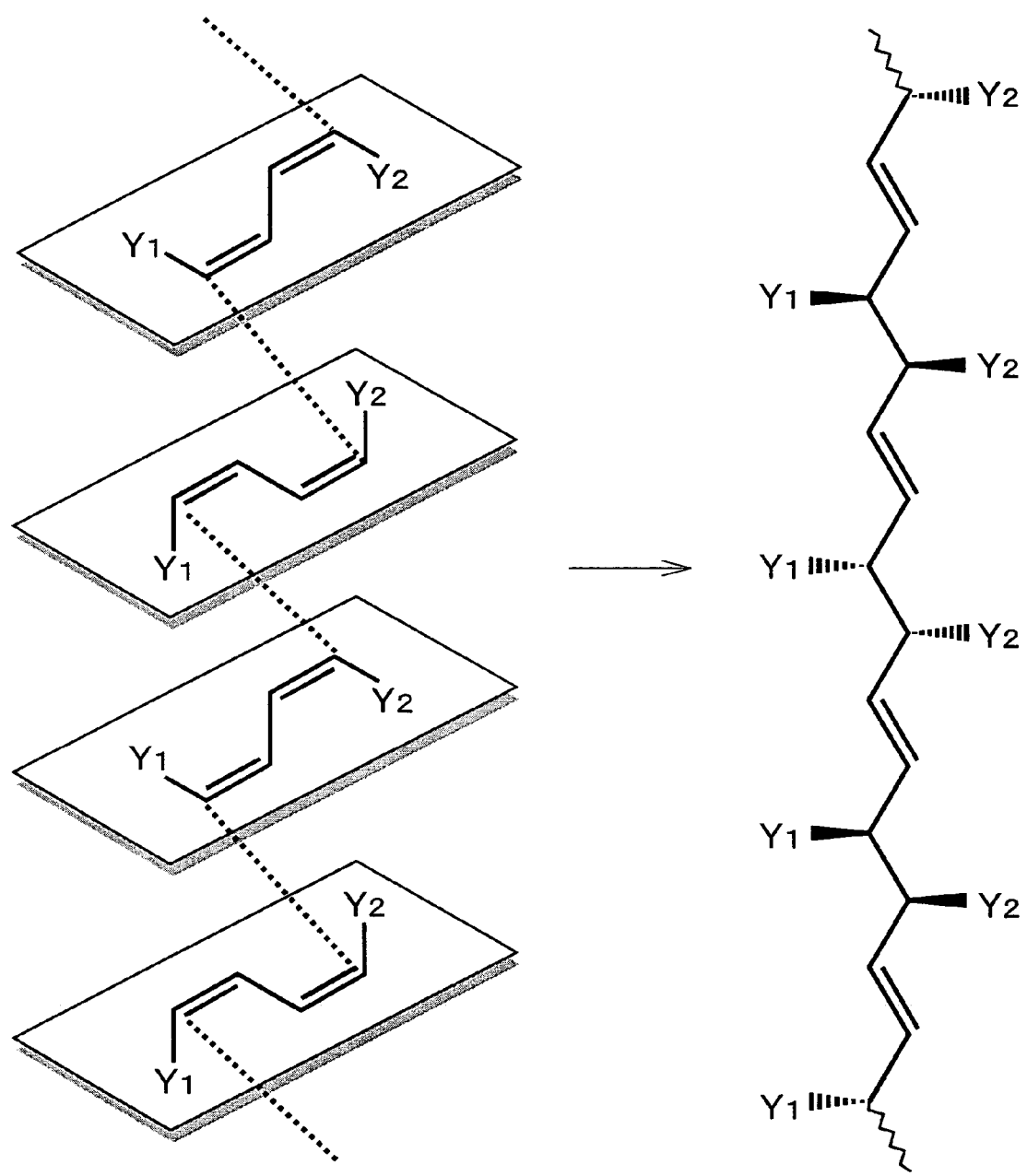
FIG. 12 is a conceptual diagram illustrating structures of a stereoregular polymer of a disyndiotactic structure and the monomer thereof.

Further, disyndiotactic polymer was also obtained through various method other than the foregoing method. FIG. 10 shows other polymerization methods produced disyndiotactic polymer.

the ester substituent produced diisotactic polymer, even though the ester substituent has the same methoxy group. Accordingly, it is preferably that the ester substituent is 4-methoxy benzyl or 4-ethoxy benzyl.

INDUSTRIAL APPLICABILITY

As described, the stereoregular polymer of the present invention is obtained through polymerization of an ester derivant, comprising the step of: forming a lamination crystal structure using a carboxylic acid having a carbon-carbon double bond and a compound having a functional group that can react to a carboxyl group of the carboxylic acid, so that molecules in two adjacent molecule planes are antiparallel.

More preferably, the ester derivant is produced by reacting a carboxylic acid having a carbon-carbon double bond with a compound having a functional group that can react to

TABLE 10

| STRUCTURE OF MONOMER | ESTER SUBSTITUENT | STRUCTURE OF POLYMER | IRRADIATION METHOD | YIELD (%) |
|---|---|---|---|---|
| (Z, Z)- | 4-METHOXYBENZYL | DISYNDIOTACTIC | ULTRAVIOLET LIGHT | 93 |
| (Z, Z)- | 4-ETHOXYBENZYL | DISYNDIOTACTIC | ULTRAVIOLET LIGHT | 95 |
| (E, E)- | 4-METHOXYBENZYL | DISYNDIOTACTIC | ULTRAVIOLET LIGHT | 81 |
| (E, E)- | 4-ETHOXYBENZYL | DISYNDIOTACTIC | ULTRAVIOLET LIGHT | 63 |
| (Z, Z)- | 4-METHOXYBENZYL | DISYNDIOTACTIC | γ RAY | 100 |
| (Z, Z)- | 4-ETHOXYBENZYL | DISYNDIOTACTIC | γ RAY | 100 |
| (E, E)- | 4-METHOXYBENZYL | DISYNDIOTACTIC | γ RAY | 100 |
| (E, E)- | 4-ETHOXYBENZYL | DISYNDIOTACTIC | γ RAY | 100 |
| (E, Z)- | 4-METHOXYBENZYL | DISYNDIOTACTIC | γ RAY | 96 |
| (E, E)- | 3-METHOXYBENZYL | DIISOTACTIC | ULTRAVIOLET LIGHT | 67 |
| (E, E)- | 3-METHOXYBENZYL | DIISOTACTIC | γ RAY | 100 |

As shown in Table 10, in polymerization of (Z, Z)—muconic acid di(4-methoxy benzyl) and (E, E)-muconic acid di(4-methoxy benzyl), disyndiotactic polymer was obtained either by irradiation of ultraviolet light for 8 hours at a room temperature or by irradiation of γ ray (200 kGy) at a room temperature.

Further, also in polymerization of (E, Z)-muconic acid di(4-methoxy benzyl), disyndiotactic polymer was obtained through irradiation of γ ray. Here, powder X-ray diffraction spectrum of the crystals of (E, Z)-muconic acid di(4-methoxy benzyl) and the disyndiotactic polymer (polymer from (E, Z form) were measured (FIG. 10). It has shown that the crystalline property is kept through the polymerization from monomer to polymer.

Further, disyndiotactic polymer was also obtained through polymerization of the crystal of (Z, Z) or (E, E)-muconic acid di(4-methoxy benzyl) ester that contains 4-ethoxybenzyl as an ester substituent. Note that, the polymerization here was performed in the same manner as that above, either by irradiation of ultraviolet light for 8 hours at a room temperature or by irradiation of γ ray (200 kGy) at a room temperature.

Note that, the polymerization reaction and the structure of polymer may change depending on the position of the ester substituent. Therefore, as shown in Table 10, the polymerization using (E, E)-muconic acid di(3-methoxy benzyl) as a carboxyl group of the carboxylic acid, using hexamethylphospholamide as a solvent, in the presence of a potassium carbonate.

With this method, an ester derivant with specific stereoregularity can be obtained at a higher rate while suppressing isomerization of the product. Namely, the foregoing esterification carries out reaction with secure acquirement of an ester derivant having a specific configuration among the ester derivants at a high selectivity.

The stereoregular polymer of the present invention can be easily obtained by polymerizing a crystal of the ester derivant either by light irradiation or heating.

Since the stereoregular polymer of the present invention has a disyndiotactic structure, it is superior in crystallization, mechanical characteristic, solvent resistance, thermostability. Therefore, the polymer can be used as a desirable material of an engineering plastic etc.

The invention claimed is:

1. A stereoregular polymer of a disyndiotactic structure with hydrocarbon chain repeating units denoted by a general formula (1):

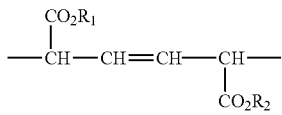 (1)

wherein each of $R_1$ and $R_2$ is $R_5$ denoted by the following general formula

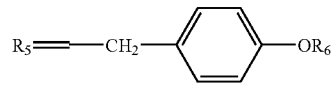

where $R_6$ is a hydrocarbon group.

2. A production method of a stereoregular polymer, wherein said method comprises polymerizing a crystal of an ester derivant either by light irradiation or heating, wherein the ester derivant has a carbon-carbon double bond and has a lamination crystal structure, wherein molecules in two adjacent molecule planes are antiparallel, and wherein the ester derivant has a structure denoted by a general formula (4),

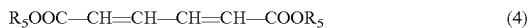 (4)

where $R_5$ is denoted by the following general formula,

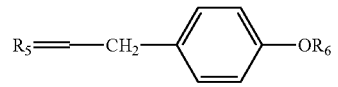

where $R_6$ is a hydrocarbon group.

* * * * *